United States Patent
Wang et al.

(10) Patent No.: US 9,555,130 B2
(45) Date of Patent: Jan. 31, 2017

(54) COMPOSITIONS AND METHODS FOR IN VIVO IMAGING OF MYELIN IN THE PERIPHERAL NERVOUS SYSTEM

(75) Inventors: Yanming Wang, Beachwood, OH (US); Chunying Wu, Beachwood, OH (US)

(73) Assignee: Case Western Reserve University, Cleveland, OH (US)

( * ) Notice: Subject to any disclaimer, the term of this patent is extended or adjusted under 35 U.S.C. 154(b) by 621 days.

(21) Appl. No.: 13/284,288

(22) Filed: Oct. 28, 2011

(65) Prior Publication Data
US 2012/0093727 A1    Apr. 19, 2012

Related U.S. Application Data

(63) Continuation-in-part of application No. 12/675,248, filed on Feb. 25, 2010.

(60) Provisional application No. 61/407,559, filed on Oct. 28, 2010.

(51) Int. Cl.
*A61K 51/00* (2006.01)
*A61M 36/14* (2006.01)
*A61K 49/00* (2006.01)

(52) U.S. Cl.
CPC .................................. *A61K 49/0021* (2013.01)

(58) Field of Classification Search
None
See application file for complete search history.

(56) References Cited

U.S. PATENT DOCUMENTS 6,168,776 B1 * 1/2001 Klunk et al. ................. 424/1.11
2006/0108509 A1 * 5/2006 Frangioni et al. .......... 250/208.1
2010/0068140 A1 * 3/2010 Hehir et al. ................. 424/1.89

FOREIGN PATENT DOCUMENTS

WO    WO 2008042486 A2 * 4/2008

OTHER PUBLICATIONS

Wu et al. J. Histochem. Cytochem. 2006, 54(9), 997-1004.*
Stankoff et al. PNAS, 2006 103(24, 9304-9309.*
Bhushan et al. Angew. Chem. Int. Ed. 2007, 46, 7969-7971.*
Quarles et al. Basic Neurochemistry: Molecular, Cellular and Medical Aspects 2005, 51-71.*
Halldin et al. Curr. Radiopharm. Des. 2001, 7, 1907-1929.*

* cited by examiner

*Primary Examiner* — Michael G Hartley
*Assistant Examiner* — Sean R Donohue
(74) *Attorney, Agent, or Firm* — Tarolli, Sundheim, Covell & Tummino LLP (57) ABSTRACT

A method of detecting and/or labeling myelin in an animal's peripheral nervous system tissue includes administering to the animal a fluorescent stilbenzene derivative and visualizing the animal's peripheral nervous system tissue using an in vivo imaging modality.

16 Claims, 5 Drawing Sheets

COMPOSITIONS AND METHODS FOR IN VIVO IMAGING OF MYELIN IN THE PERIPHERAL NERVOUS SYSTEM

RELATED APPLICATION

This application claims priority from U.S. Provisional Application No. 61/407,559, filed Oct. 28, 2010, and is a continuation-in-part of U.S. patent application Ser. No. 12/675,248, filed Feb. 25, 2010, the subject matter of which is incorporated herein by reference in their entirety.

TECHNICAL FIELD

This application relates to molecular probes and to methods of their use, and particularly relates to molecular probes that selectively localize in the myelinated regions of the peripheral nervous system.

BACKGROUND OF THE INVENTION

Information flow within the nervous system requires the perpetuation of ionic gradients along neurons. In many neurons, effective and efficient perpetuation of such gradients along axons requires electrical insulation. Myelin is a specialized lipid-rich, dielectric substance that ensheathes neuronal axons that serves this insulating function, promoting efficient nerve impulse transmission (Morell and Quarles (1999) Basic Neurochemistry: molecular, cellular, and medical aspects. In Siegel G J, ed. Myelin Formation, Structure, and Biochemistry. Lippincott-Raven Publishers, 79-83). The nervous system contains high levels of myelin, which is especially enriched where many myelinated axons are bundled together, such as in tracts of the spinal cord and spinal nerve roots, nerves in the peripheral nervous system, and fiber tracts in the brain, collectively called "white matter" (as opposed to "grey matter"). Because non-nervous system tissue lacks myelin, the presence of myelin can distinguish peripheral nerve tissue from other tissue types, the spinal cord and spinal nerve roots from non-nervous elements of the vertebral column, and white matter from grey matter.

Due to its important biological functions in the nervous system and its vulnerability in disease, several techniques have been developed to visualize and characterize myelin histopathology. These can be broadly divided into those based upon antibody immunohistochemistry (IHC) (Horton and Hocking (1997) Cereb. Cortex 7:166-177) and more traditional histochemical procedures. The classic histochemical stains include luxol fast blue MBN (Kluver and Barrera (1953) J Neurosci Methods 153: 135-146; Presnell and Schreibman (1997) Humanson's Animal Tissue Techniques, 5$^{th}$ ed.; Kiernan (1999) Histological and Histochemical Methods: Theory and practice, 3$^{rd}$ ed.; Bancroft and Gamble (2002), Theory and Practice of Histological Techniques, 5 ed. and Sudan Black B (Lison and Dagnelie (1935) Bull. d'Histologie Appliquee 12: 85-91). Traditional chromogenic methods also include the Palweigert method ((Weigert (1884) Fortschr Deutsch Med 2: 190-192, (1885) Fortschr Deutsch Med 3:236-239; Clark and Ward (1934) Stain Technol 54:13-16), the Weil stain (Weil (1928) Arch Neurol Psychiatry 20:392-393; Berube et al. (1965) Stain Technol 40:53-62)), the Loyez method (Cook (1974) Manual of Histological Demonstration Methods, 5$^{th}$ ed.), and a method based on horse serum followed by subsequent reaction with diaminobenzidine (McNally and Peters (1998) J Histochem Cytochem 46:541-545). In addition, modified silver stains including the Gallyas method (Pistorio et al. (2005) J Neurosci Methods 153: 135-146) and Schmued's gold chloride technique (Schmued and Slikker (1999) Brain Res 837:289-297) have also been used as simple, high-resolution histochemical markers of myelin. More recently, fluoromyelin (Kanaan et al. (2005) Am J Physiol Regul Integr Comp Physiol 290:R1105-1114) and NIM (Xiang et al. (2005) J Histochem Cytochem 53:1511-1516) were introduced as novel myelin dyes, which enable quick and selective labeling of myelin including brain tissue sections. In addition, fluorescent stilbenzene derivative have been shown to selectively bind to myelin in an animal's brain tissue (Wu et al., (2006) J Histochem Cytochem 54: 997-1004).

However, the lack of in vivo molecular probes has limited the progress of peripheral nervous system tissue myelin imaging and hindered efficacy evaluation of novel peripheral nervous system tissue myelin repair therapies during their development.

SUMMARY

This application relates to a method of detecting, identifying, and/or labeling myelin in vivo in an animal's peripheral nervous system tissue. The method includes administering in vivo to the animal a molecular probe that includes a compound having the general formula:

wherein $R_1$ and $R_2$ are each independently a hydrophilic or lipophilic group; wherein $X_1$ and $X_2$ are each independently a double or triple bond; and each $R_4$—$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', N(R')$_2$, NO$_2$, (C=O)N(R')$_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group) or a salt thereof. In one embodiment, $R_1$ and/or $R_2$ can be selected from the group consisting of H, NO$_2$, NH$_2$, NHCH$_3$, N(CH$_3$)$_2$, OH, OCH$_3$, COOCH$_3$, SH, SCH$_3$, and alkyl derivatives thereof and each $R_4$-$R_{13}$ is H. Following administration of the molecular probe, the animal's peripheral nervous system tissue is visualized using an in vivo imaging modality.

The application further relates to a method of detecting a myelin related disorder in a subject. The method includes labeling myelin in vivo in the animal's peripheral nervous system tissue by administering to the animal a molecular probe that includes a compound having the general formula:

wherein $R_1$ and $R_2$ are each independently a hydrophilic or lipophilic group; wherein $X_1$ and $X_2$ are each independently a double or triple bond; and each $R_4$-$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', N(R')$_2$, NO$_2$, (C=O)N(R')$_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group) or a salt thereof. In one aspect one embodiment, $R_1$ and/or $R_2$ can be selected from the group consisting of H, NO$_2$, NH$_2$, NHCH$_3$, N(CH$_3$)$_2$, OH, OCH$_3$, COOCH$_3$, SH, SCH$_3$, and alkyl derivatives thereof and each $R_4$-$R_{13}$ is H. The distribution of the molecular probe in the animal's peripheral nervous system tissue is then visualized. The distribution of the molecular probe can then be correlated with a myelin related disorder in the animal.

The application further relates to a method of monitoring the efficacy of a remyelination therapy in an animal. The method includes labeling myelin in vivo in the animal's peripheral nervous system tissue with a molecular probe having the general formula wherein $R_1$ and $R_2$ are each independently a hydrophilic or lipophilic group; wherein $X_1$ and $X_2$ are each independently a double or triple bond; and each $R_4$-$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', N(R')$_2$, NO$_2$, (C=O)N(R')$_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group) or a salt thereof. In one embodiment, $R_1$ and/or $R_2$ can be selected from the group consisting of H, NO$_2$, NH$_2$, NHCH$_3$, N(CH$_3$)$_2$, OH, OCH$_3$, COOCH$_3$, SH, SCH$_3$, and alkyl derivatives thereof and each $R_4$—$R_{13}$ is H. A distribution of the molecular probe in the animal's peripheral nervous system tissue is visualized. The distribution of the molecular probe can then be correlated with the efficacy of the remyelination therapy.

The application also relates to a method of screening the myelination effects of an agent in an animal. The method includes labeling myelin in vivo in the animal's peripheral nervous system tissue with a molecular probe having the general formula:

wherein $R_1$ and $R_2$ are each independently a hydrophilic or lipophilic group; wherein $X_1$ and $X_2$ are each independently a double or triple bond; and each $R_4$-$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', N(R')$_2$, NO$_2$, (C=O)N(R')$_2$, O(CO)R', OR', SR', COOR', $R_{ph}$, CR'=CR'—$R_{ph}$, $CR_2'$—$CR_2'$ —$R_{ph}$ (wherein $R_{ph}$ represents an unsubstituted or substituted phenyl group, wherein R' is H or a lower alkyl group) or a salt thereof. In one embodiment, $R_1$ and/or $R_2$ can be selected from the group consisting of H, NO$_2$, NH$_2$, NHCH$_3$, N(CH$_3$)$_2$, OH, OCH$_3$, COOCH$_3$, SH, SCH$_3$, and alkyl derivatives thereof and each $R_4$-$R_{13}$ is H. A distribution of the molecular probe in the animal's peripheral nervous system tissue is visualized. The distribution of the molecular probe can then be correlated with the myelination effects of the agent. In one example, the distribution of the molecular probe in the animal's peripheral nervous system tissue can be compared to a distribution of the molecular probe in a control population to determine the efficacy of the agent.

The application further relates to a method of imaging myelinated tissue at a surgical site in an animal. The method includes labeling myelin in vivo at the surgical site of the animal with a molecular probe having the general formula:

wherein $R_1$ and $R_2$ are each independently a hydrophilic or lipophilic group; wherein $X_1$ and $X_2$ are each independently a double or triple bond; and each $R_4$-$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', N(R')$_2$, NO$_2$, (C=O)N(R')$_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group) or a salt thereof. In one embodiment, $R_1$ and/or $R_2$ can be selected from the group consisting of H, NO$_2$, NH$_2$, NHCH$_3$, N(CH$_3$)$_2$, OH, OCH$_3$, COOCH$_3$, SH, SCH$_3$, and alkyl derivatives thereof and each $R_4$-$R_{13}$ is H. Following administration of the molecular probe, the surgical site of the animal is visualized using an in vivo imaging modality.

BRIEF DESCRIPTION OF THE DRAWINGS

The foregoing and other features and advantages of the application will become apparent to those skilled in the art to which the present invention relates upon reading the following description with reference to the accompanying drawings, in which.

DETAILED DESCRIPTION

The definitions provided herein are to facilitate understanding of certain terms used frequently herein and are not meant to limit the scope of the application.

The term "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes that retain the desired biological activity of the parent compound and exhibit minimal, if any, undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

An agent exhibits "specific binding" or "selective binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or nonspecific binding, each sample should be measured under similar physical conditions (i.e., temperature, pH, and solvent). Generally, specific binding is characterized by a relatively high affinity of an agent to a receptor and a relatively low to moderate capacity. Typically, binding is considered specific when the affinity constant Ka is at least $10^6$ $M^{-1}$. A higher affinity constant indicates greater affinity, and thus typically greater specificity. For example, antibodies typically bind antigens with an affinity constant in the range of $10^6$ $M^{-1}$ to $10^9$ $M^{-1}$ or higher. "Non-specific" binding usually has a low affinity with a moderate to high capacity. Non-specific binding usually occurs when the affinity constant is below $10^6$ $M^{-1}$. Controlling the time and method used to contact the agent with the tissues reduces non-specific binding.

The phrase "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

As used herein, the phrase "remyelination" refers to the spontaneous, therapeutic, or experimentally induced repair, regeneration, or otherwise enhanced constitution or functionality of the insulating material ensheathing neuronal axons.

As used herein, the phrase "molecular imaging" refers to a non-invasive technique for in vivo imaging of biological targets at molecular level. Molecular imaging can involve the targeting of a biomarker with a molecular probe.

As used herein, the phrase "molecular probe" refers to a compound that specifically binds to a biomarker (e.g., myelin), allowing for the imaging and studying of the marker. As used herein, the phrase "biomarker" refers to a biological substance that is specific to a certain biological process or mechanism.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

This application relates to a method of detecting, identifying, and/or labeling myelin in vivo in an animal's peripheral nervous system tissue. It was found that upon administration to a mammal (e.g., systemic, parenteral, or intravenous administration), a molecular probe comprising a fluorescent stilbenzene derivative can selectively localize and bind to myelinated regions of the peripheral nervous system. The molecular probe can be readily visualized using conventional visualization techniques to detect, identify, and/or label myelinated regions of the peripheral nervous system and tissues thereof.

In some embodiments, the molecular probe described herein may be detected by its emitted signal, such as a magnetic resonance signal or emitted radiation from a radioisotope, autofluorescence emission, or optical properties. It is further contemplated that the molecular probes can be used in a method of detecting a level of myelination in vivo in the peripheral nervous system of a subject, a method of detecting a myelin related disorder in the peripheral nervous system of a subject, a method of monitoring the remyelination effects of an agent in the peripheral nervous system of a subject, a method of screening the myelination effects of an agent in the peripheral nervous system of a subject, and a method of imaging myelinated tissue at a surgical site in the peripheral nervous system of a subject.

In an embodiment of the application, the molecular probe can include a fluorescent stilbenzene derivative that is less than about 700 daltons and has a relatively high binding affinity (Kd) (e.g., at least about 100 nM) to isolated myelin fractions but a relatively low binding affinity (Kd) (e.g., up to about 10 μM) to isolated non-myelin fractions. The fluorescent stilbenzene derivative can have an excitation spectra at a wavelength of about 300 nm to about 500 nm (emission at 506 nm) and emission spectra upon exciting at a wavelength of about 430 nm to about 650 nm (excitation at 426 nm).

In another embodiment of the application, the molecular probe can include a fluorescent stilbenzene derivative having the following formula:

wherein $R_1$ and $R_2$ are each independently a hydrophilic or lipophilic group; wherein $X_1$ and $X_2$ are each independently a double or triple bond; and each $R_4$-$R_{13}$ is independently selected from the group consisting of H, F, Cl, Br, I, a lower alkyl group, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, (C=O—R', $N(R')_2$, $NO_2$, (C=O)$N(R')_2$, O(CO)R', OR', SR', COOR', $R_{ph}$, CR=CR'—$R_{ph}$, $CR_2'$—$CR_2'$—$R_{ph}$ (wherein $R_{ph}$ represents an unsubstituted or substituted phenyl group, wherein R' is H or a lower alkyl group) or a salt thereof.

In some embodiments, $R_1$ and/or $R_2$ can be selected from the group consisting of H, $NO_2$, $NH_2$, $NHCH_3$, $N(CH_3)_2$, OH, $OCH_3$, $COOCH_3$, SH, $SCH_3$, and alkyl derivatives thereof and each $R_4$-$R_{13}$ is H.

In other embodiments, the molecular probe can include a fluorescent stilbenzene derivative having the following formula:

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof or a salt thereof.

In still other embodiments, the molecular probe can include a fluorescent stilbenzene derivative having the following formula:

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof or a salt thereof.

In certain embodiments, the molecular probe can be a (E,E)-1,4-bis(4'-aminostyryl)-2-dimethoxy-benzene (BDB) which has the following general structure:

or a salt thereof.

The foregoing formulae represent the general structures of fluorescent stilbenzene compounds found to be effective molecular probes for labeling myelin in vivo as well as in vitro as described in the examples below. They are characterized by their ability to selectively localize in the myelinated regions of the peripheral nervous system via direct binding to myelin membranes and not bind to degenerating myelin fragments.

When referring to the terms "molecular probe", "fluorescent stilbenzene compound" or "compound" in the specification and the claims, it is intended that the terms encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

Typically, the molecular probe employed in the inventive method can be formulated into solution prior to use. In one example, a molecular probe solution includes a 10 mM molecular probe solution. A molecular probe solution can also contain saline, DMSO, and HCl. One skilled in the art can utilize the molecular probe with pharmaceutical carriers and/or excipients in varying concentrations and formulations depending on the desired use.

In some embodiments, a molecular probe described above may be used without modification and is capable of being visualized using fluorescence imaging. In some embodiments of the present invention, the molecular probe can be radiolabeled to aid in the detection of the molecular probe once it binds to myelin. A 'radiolabel' as used herein is any compound that has been joined with a radioactive substance. Examples of radiolabels include positron emitting $^{11}$C and $^{18}$F radiolabels.

In an embodiment of the application, the molecular probe can be coupled to a chelating group (with or without a chelated metal group) to improve the magnetic resonance imaging (MRI) contrast properties of the molecular probe. In one example, as disclosed in U.S. Pat. No. 7,351,401 which is herein incorporated by reference in its entirety, the chelating group can be of the form W-L or V-W-L, wherein V is selected from the group consisting of —COO—, —CO—, —CH$_2$O— and —CH$_2$NH—; W is —(CH$_2$)n where n=0,1,2,3,4, or 5; and L is:

wherein M is selected from the group consisting of Tc and Re; or wherein each R$_3$ is independently is selected from one of:

or a myelin binding, chelating compound (with or without a chelated metal group) or a water soluble, non-toxic salt thereof of the form:

-continued wherein each $R_3$ independently is selected from one of:

The chelating group can be coupled to the central benzene group, at least one terminal benzene groups, or the R1 or R2 groups. In one example, the chelating group can be coupled to terminal amino R1 and/or R2 group through carbon chain link. The carbon chain link can comprise, for example about 2 to about 10 methylene groups and have a formula of, for example, (CH2)n, wherein n=2 to 10.

In some embodiments, the molecular probe with the chelating group can have the following formula:

wherein $X_3$ is a chelating group and n is 2 to 10; or a salt thereof.

In other embodiments, the molecular probe with the chelating group can have the following formula:

wherein $X_3$ is a chelating group and n is 2 to 10; or a salt thereof.

In still other embodiments, the molecular probe with the chelating group can have the following formula:

wherein $X_3$ is a chelating group and n is 2 to 10; or a salt thereof.

In another embodiment, a molecular probe can be coupled to a near infrared group to improve the near infrared imaging of the molecular probe. Examples of near infrared imaging groups that can be coupled to the molecular probe include:

Cyanine 5

These near infrared imaging groups are disclosed in, for example, Tetrahedron Letters 49(2008) 3395-3399; Angew. Chem. Int. Ed. 2007, 46, 8998-9001; Anal. Chem. 2000, 72, 5907; Nature Biotechnology vol 23, 577-583; Eur Radiol (2003) 13: 195-208;and Cancer 67: 1991 2529-2537, which are herein incorporated by reference in their entirety.

The near infrared imaging group can be coupled to the central benzene group, at least one terminal benzene groups, or the $R_1$ or $R_2$ groups. In one example, the near infrared imaging group can be coupled to at least one terminal benzene group.

In one example, the molecular probe with the near infrared imaging group can have the following formula:

wherein NIR is a near infrared imaging group; or a salt thereof.

By way of example, the molecular probe can include a compound having the following formula:

wherein n is 3 to 10; or a salt thereof.

In another embodiment, the molecular probe with the chelating group can have the following formula:

wherein NIR is a near infrared imaging group; or a salt thereof.

In certain embodiments, the molecular probes described herein can be contacted with an animal's (or subject's) peripheral nervous system tissue and utilized for labeling, detecting, and/or identifying myelinated regions of an animal's peripheral nervous system. Myelinated regions of an animal's peripheral nervous system tissue are typically found in nerves and ganglia outside of the brain and the spinal cord in the myelin sheaths of neuronal axons. Myelin is an outgrowth of glial cells, more specifically oligodendrocytes, which serve as an electrically insulating phospholipid layer surrounding axons of many neurons. The animal or subject, as used herein, can be a mammal, such as a primate, e.g., chimpanzee or human; cow; dog; cat; a rodent, e.g., guinea pig, rat, mouse; rabbit; or a bird; reptile; or fish.

In some embodiments, the molecular probes described herein can be used for the in vivo labeling, detection, identification, and localization of myelinated regions of an animal's (or subject's) peripheral nervous system. The molecular probe can be administered to the animal or subject as per the examples contained herein, but typically through intravenous injection. "Administered", as used herein, means provision or delivery of molecular probes in an amount(s) and for a period of time(s) effective to label myelin in an animal's peripheral nervous system tissue. The molecular probes administered to the animal can be enterally or parenterally administered in a solid or liquid. Enteral route includes oral, rectal, topical, buccal, and vaginal administration. Parenteral route includes intravenous, intramuscular, intraperitoneal, intrasternal, and subcutaneous injection or infusion.

An example of a dosing regimen is to administer about 40- about 50 mg/kg by weight to the animal. In one example at 5 min, the concentration of molecular probe in a peripheral nervous system tissue can range between about 4% to about 24% Injected Dose per Gram of Tissue (ID/g) to ensure sufficient visualization of the myelinated regions of the peripheral nervous system tissue.

Methods described herein can be used in analytical, diagnostic, or prognostic applications related to myelin detection. The inventive methods may be particularly applicable in intraoperative nerve labeling, spinal imaging, non-invasive in vivo measurement of myelination levels, and preclinical and basic neuroscience bench research aimed at the study of the function and process of myelination, and the dysfunction and repair of myelin. In some embodiments, researchers studying normal peripheral nervous system tissue can employ this method to examine the morphology and distribution of myelinated tissue in an animal. "Distribution" as used herein is the spatial property of being scattered about over an area or volume. In this case the "distribution of myelinated tissue" is the spatial property of myelin being scattered about over an area or volume included in the animal's peripheral nervous system tissue. Researchers interested in neurotoxicology and neuropathology can also use this method in several ways. One way is to infer demyelination by the absence of the molecular probe labeling compared to normal control tissue. A second way is to study morphological changes in the myelin, such as a fragmented or beaded appearance of the myelin sheath. In yet another embodiment of the present invention, one skilled in the art can assess and quantify changes in myelin content in vivo.

In other aspects of the present invention, myelin in an animal's peripheral nervous system tissue can be visualized and quantified using an in vivo imaging modality. The molecular probe may be visualized any time post administration depending on the application as typical molecular probes embodied in the present invention have a low clearance rate due to specific binding in the myelinated regions (e.g., at 60 min, the PNS tissue concentration of probe can be ≤50% of 5 min value to ensure that half time retention in normally myelinated peripheral nervous system tissue is 60 min or longer).

An in vivo imaging modality can be an imaging modality capable of visualizing molecular probes described herein in vivo (within a living organism). In some aspects, an imaging modality can be capable of visualizing a molecular probe described above utilizing the specific binding to myelin of the molecular probes, and their autofluorescence, or the radioactive signal emitted by a radioisotope derivative thereof.

An example of an in vivo imaging modality employed herein is positron emission tomography (PET). PET is a functional imaging technique that can detect chemical and metabolic change at the molecular level. To function as a PET imaging molecular probe, a molecular probe must meet a set of biological requirements known to the skilled artisan, some of which may include lipophilicity, binding affinity, binding specificity, tissue uptake, retention, and metabolism. Another example of an in vivo imaging modality is Micro-PET. MicroPET is a high resolution positron emission tomography scanner designed for imaging small laboratory animals. Other examples of imaging modalities that can be employed include magnetic resonance imaging (MRI), near infrared (NIR) imaging, magnetic resonance spectroscopy ("MRS"), computed tomography ("CT"), single photon emission computed tomography ("SPECT")fluorescent luminescence imaging (FLI), laser-confocal microscopy, cross-polarization microscopy, nuclear scintigraphy, fluorescent microscopy, multiphoton microscopy or a combination thereof, depending on the intended use and the imaging methodology available to the medical or research personnel.

Molecular probes described herein can directly bind to the peripheral nervous system tissue in proportion to the extent of myelination and can be used to monitor the degree, level, and/or distribution of myelin in the peripheral nervous system. In certain embodiments, radiolabeled molecular probes described herein can be used in conjunction with PET as imaging markers to directly assess the extent of total lesion volumes associated with demyelination. This can provide a direct clinical efficacy endpoint measure of myelin changes and identify effective therapies aimed at protection and repair of axonal damages.

In some embodiments, the molecular probe can be used in a method of diagnosing a myelin related disorder in an animal. The method can include labeling myelin in vivo in the animal's peripheral nervous system tissue with a molecular probe described herein, visualizing a distribution of the molecular probe in the animal's peripheral nervous system tissue as described above and in the examples, and then correlating the distribution of the molecular probe with a myelin related disorder in the animal. In one example, the method described herein can be used to compare myelinated axonal regions of a nerve in the normal tissues of control populations to those of an animal suspected of having a myelin related disorder. If the suspect animal has a myelin related disorder, myelin may be virtually absent in lesioned areas thus indicating the presence of a myelin related disorder.

Myelin related disorders detected herein can include can include any disease, condition (e.g., those occurring from traumatic nerve injury and infarction), or disorder related to demylination, remylination, or dysmyelination in an animal. A myelin related disorder may result from a variety of neurotoxic insults, autoimmune diseases, genetic diseases, metabolic/endocrine disorders, inflammatory diseases, along with enzyme and/or vitamin deficiencies. For example, leukodystrophies are caused by inherited enzyme deficiencies, which cause abnormal formation, destruction, and/or abnormal turnover of myelin sheaths within the peripheral nervous system tissue.

In some embodiments, the myelin related disorder detected can include a demyelination related disorder of the peripheral nervous system. A demyelination related disorder of the peripheral nervous system generally refers to any disorder in which the insulating material ensheathing portions of neuronal cells becomes damaged or dysfunctional as a component of a syndrome, disease, or other pathological condition, such as, but not limited to, Guillain-Barre syndrome, chronic inflammatory demyelinating polyneuropathy (CIDP), Charcot-Marie-Tooth disease (CMT), anti-MAG peripheral neuropathy, leukodystrophies, diabetic neuropathy, chemotherapy induced neuropathy, or any combination thereof. In some embodiments, a demyelination related disorder of the peripheral nervous system can include a demyelination related disorder of the somatic nervous system, autonomic nervous system and/or the enteric nervous system.

Another embodiment of the application, relates to a method of monitoring the efficacy of a remyelination therapy in an animal. Remyelination is the repair of damaged or replacement of absent myelin in an animal's peripheral nervous system tissue. The method includes the steps of labeling myelin in vivo in the animal's peripheral nervous system tissue with a molecular probe described herein, then visualizing a distribution of the molecular probe in the animal's peripheral nervous system tissue (e.g., with a in vivo imaging modality as described herein), and then correlating the distribution of the molecular probe as visualized in the animal's peripheral nervous system with the efficacy of the remyelination therapy. It is contemplated that the labeling step can occur before, during, and after the course of a therapeutic regimen in order to determine the efficacy of the therapeutic regimen. One way to assess the efficacy of a remyelination therapy is to compare the distribution of the molecular probe before remyelination therapy with the distribution of the molecular probe after remyelination therapy has commenced or concluded.

The term "remyelination therapy", as used herein, refers to any therapy leading to a reduction in severity and/or frequency of symptoms, elimination of symptoms and/or underlying cause, prevention of the occurrence of symptoms and/or their underlying cause, and improvement or remediation of damage related to demyelination. For example, a remyelination therapy can include administration of a therapeutic agent, therapies for the promotion of endogenous myelin repair, or a cell based therapy (e.g., a stem-cell based therapy).

In another embodiment, methods are provided for screening for a myelination response in an animal's peripheral nervous system tissue to an agent. In some embodiments, the molecular probes described herein can be used to determine if an agent of interest has the potential to modulate demyelination, remyelination, or dysmyelination of axonal regions of an experimental animal's PNS tissue.

Figure 1:
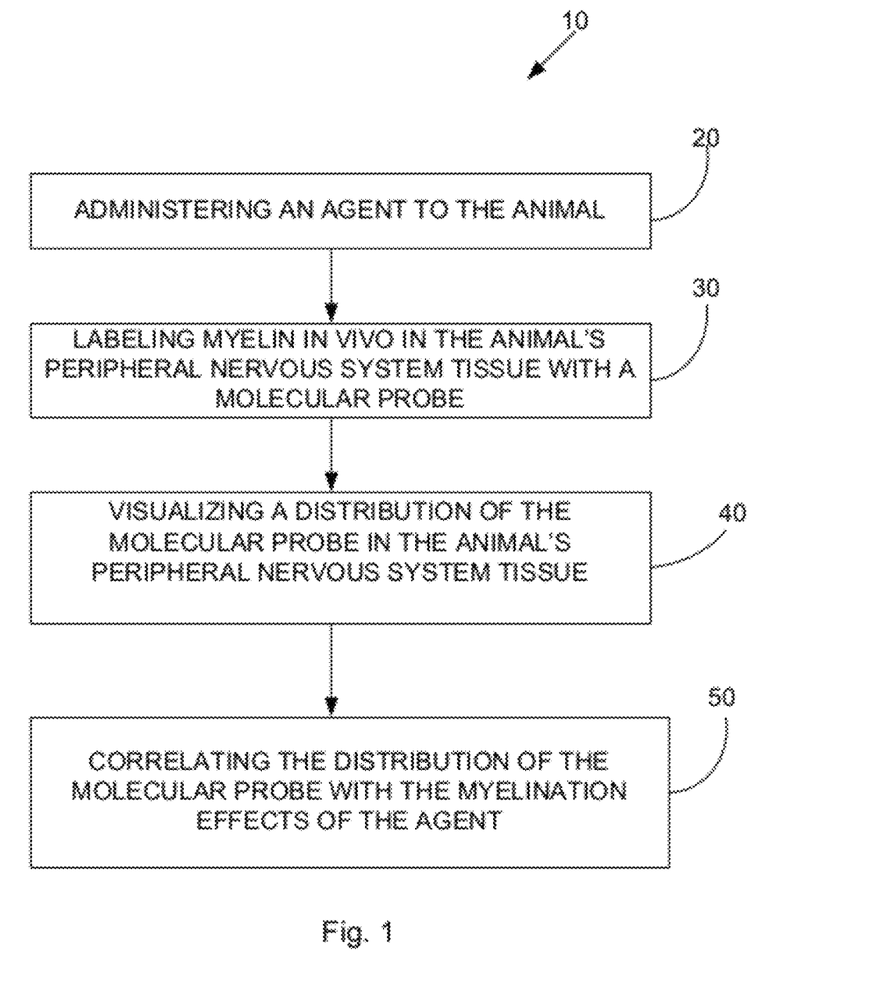
FIG. 1 illustrates a method of screening for a myelination response to an agent in an animal's peripheral nervous system (PNS) tissue.

An example of a method of screening for a myelination response in an animal's peripheral nervous system tissue to an agent is shown in FIG. 1. The method 10 includes the initial step, at 20, of administering an agent to the animal. At 30, myelin in the animal's peripheral nervous system tissue is labeled in vivo with a molecular probe in accordance with the present invention. At 40, a distribution of the molecular probe in the animal's peripheral nervous system tissue is then visualized using a conventional visualization modality. Finally, at 50, the distribution of the molecular probe in the animal's peripheral nervous tissue is correlated with the effectiveness of the myelination effects of the agent. One way to assess the myelination response in the animal's peripheral nervous system tissue is to compare the distribution of the molecular probe in an animal's peripheral nervous system tissue, which has been treated with a suspect agent with the distribution of the molecular probe in the peripheral nervous system tissue of a control.

To determine whether myelination in the animal's PNS tissue may be deficient, myelination levels or distribution may be compared to those exhibited by an animal or animals believed or known not to be suffering from a myelin related disorder. In another embodiment, rates of demyelination or remyelination may be determined. Following treatment with a known or suggested therapeutic agent believed or anticipated to prevent or slow demyelination or to promote remyelination in patients suffering from myelin related disorders, myelination levels are evaluated by performing the imaging over time in the patients treated with the therapeutic agent. The imaging may be performed at different points of time and the level of myelination at one time point compared to that of another.

In another embodiment, a biopsied animal tissue sample, or a tissue sample cultured in vitro, may be contacted with a molecular probe described above, to determine the location, presence, or amount of myelin in the tissue sample. The tissue sample may be sampled from an animal that has been experimentally manipulated so as to serve as a verified or purported model of a myelin related disorder, or that has received at least one therapeutic agent verified as, or purported to be, a treatment for a myelin related disorder. The therapeutic agent may be associated with the preclinical evaluation or basic neuroscience research aimed at studying the function and process of myelination, and the dysfunction and repair of myelin.

Fresh frozen cryostatic sections, or fixed or embedded sections or samples, of the biopsy or culture tissue sections, may be contacted with a molecular probe. The samples may be prepared using various sectioning techniques such as microtome, vibratome, or cryostat preparation. After binding to myelin, the sample may be washed in a manner and medium suitable to remove any unbound and non-specifically bound label from the sample, without eliminating specific binding to myelin.

It is further contemplated that the ability to detect and visualize myelin, either in vivo or in vitro, confers upon researchers and clinicians the ability to visually identify peripheral nerves during surgery in order to assist surgeons in avoiding cutting or damaging nerves. Therefore another aspect of the invention relates to a method of imaging myelinated tissue at a surgical site in an animal. The method includes labeling myelin in vivo at the surgical site of the animal with a molecular probe.

In one embodiment, a molecular probe or pharmaceutically described above may be administered parenterally to a surgical subject prior to surgery such that the compound binds to myelin and may be cleared from tissues that do not contain myelin. In another embodiment, a molecular probe may be applied directly to the surgical field during surgery, allowed to bind to myelin present, and the surgical site washed by lavage to clear unbound composition from the site. In some embodiments, during surgery, a light source tuned to the spectral excitation characteristics of the molecular probe may be applied to the surgical field. The molecular probe may be observed through an optical filter tuned to its spectral emission characteristics. It is contemplated by the present invention that due to the specific binding of the molecular probes to nerves and other myelin-containing nervous tissue, that the myelin-containing nervous tissue are distinguishable from tissue not containing myelin. This enables the surgeon to avoid inadvertently cutting or damaging myelinated tissue by avoiding a visually detected peripheral nervous system tissue, or facilitates accurately administering treatment targeting a nerve or other myelin containing tissue, such as pharmaceutical or surgical nerve block.

In another embodiment, a molecular probe may be administered parenterally to a patient suspected of, or determined to be, suffering from a spinal pathology, such as but not limited to, spinal compression, spinal nerve root compression, or a bulging disc. For example, after binding to spinal myelin, and clearance from tissue that does not contain myelin without eliminating the specific myelin binding, the spine may be imaged for in vivo using radioisotope imaging such as PET, SPECT, or any combination thereof.

By inspection of the diagnostic images, the clinician may determine if, and where, the spinal cord, or associated nerve roots, are impinged, such as by the vertebral column. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

EXAMPLES

Introduction

Figure 2:
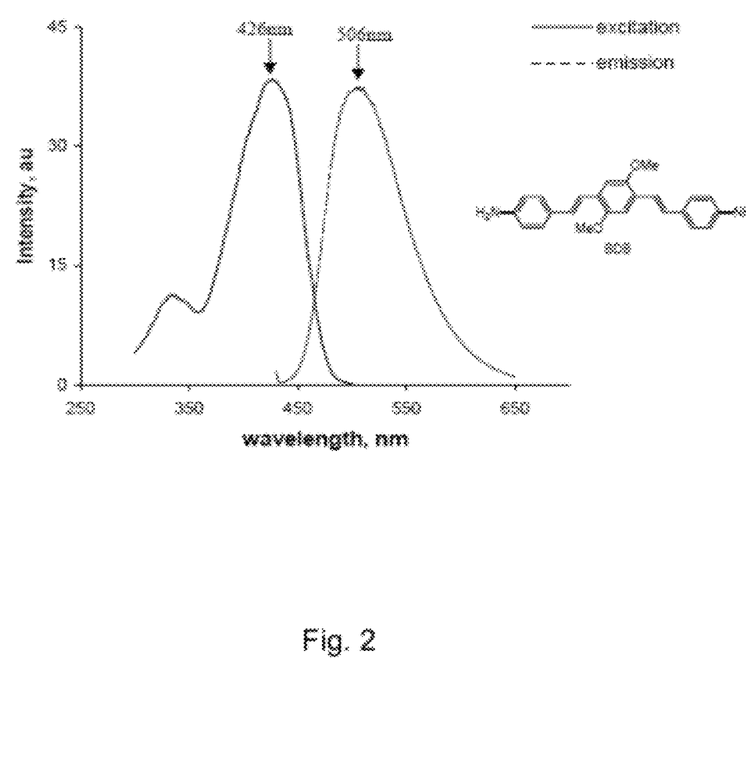
FIG. 2 illustrates excitation and emission spectra of (E,E)-1,4-bis(4-aminostyryl)-2-dimethoxy-benzene (BDB) (1 µM in DM50). Excitation spectra: emission at 510 nm (range 300-500 nm), bandwidth at 5 nm, scan at 120 nm/mm, integration time 0.5 sec. and maximal excitation wavelength at 426 nm. Emission spectra: excitation at 426 nm (range 430-650 nm), bandwidth at 5 nm, scan at 120 nm/min. integration time of 0.5 sec. and maximal emission wavelength at 506 nm.

BDB is a fluorescent compound and is soluble in $CH_2Cl_2$, DMSO, and in most other organic solvents. Excitation and emission spectra of BDB (1 μM in DMSO) recorded using a Cary Eclipse fluorescent spectrophotometer (Variant Inc.; Palo Alto, Calif.) are shown in FIG. 2. Maximal excitation and emission peaks were found at 426 nm and 506 nm, respectively.

We previously have shown that the molecular probe (E,E)-1, 4-bis(4'-aminostyryl)-2-dimethoxy-benzene (BDB), a fluorescent stilbenzene derivative, selectively binds to myelin and is retained in CNS white matter. We proposed that if BDB can bind to CNS myelin and be used as a molecular probe, then it can bind to PNS myelin due to similarities in the protein composition of the two myelin varieties. Here we show that BDB selectively stains intact myelin sheaths in peripheral nervous system tissue of wild type mice in vitro, ex vivo and in vivo.

Sciatic Nerve Imaging

The Sciatic nerve will be our representative nerve for the PNS due to its size and accessibility. This study involves three stages of research: In Vitro, Ex Vivo, and In Vivo. Imaging modalities used in the experiment include Fluorescent Microscope, Multiphoton Microscope and Fluorescence Luminescence Imaging.

In Vitro Staining Procedure: (1) Removal of wild type mouse sciatic nerve imbedded in muscle; (2) Sectioning of muscle with nerve with cryostat; (3) Chemical staining of tissue section of sciatic nerve with muscle tissue surrounded it; (4) Observation under fluorescent microscopy; (5) A Black and Gold staining of adjacent tissue section; and (6) Observation under regular microscope.

In Vitro Results

Figure 3:
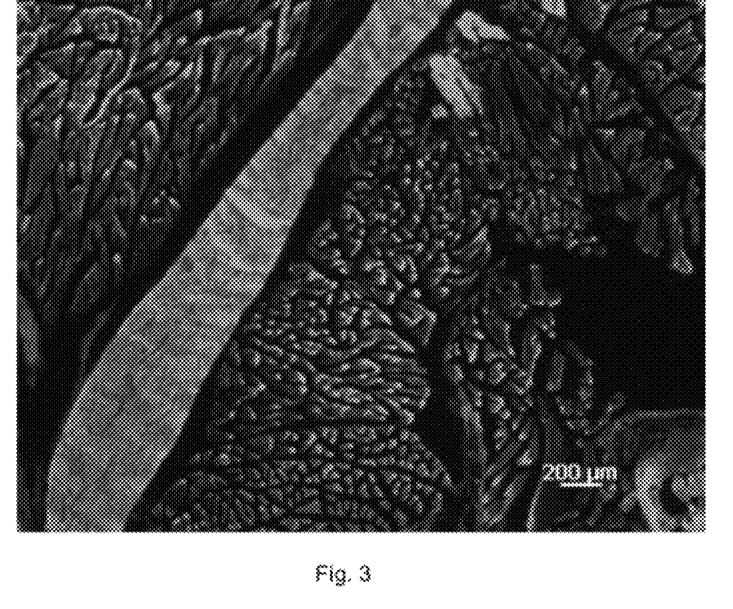
FIG. 3 illustrates photographs of in vitro BDB showing the successful staining of the sciatic nerve.
Figure 4:
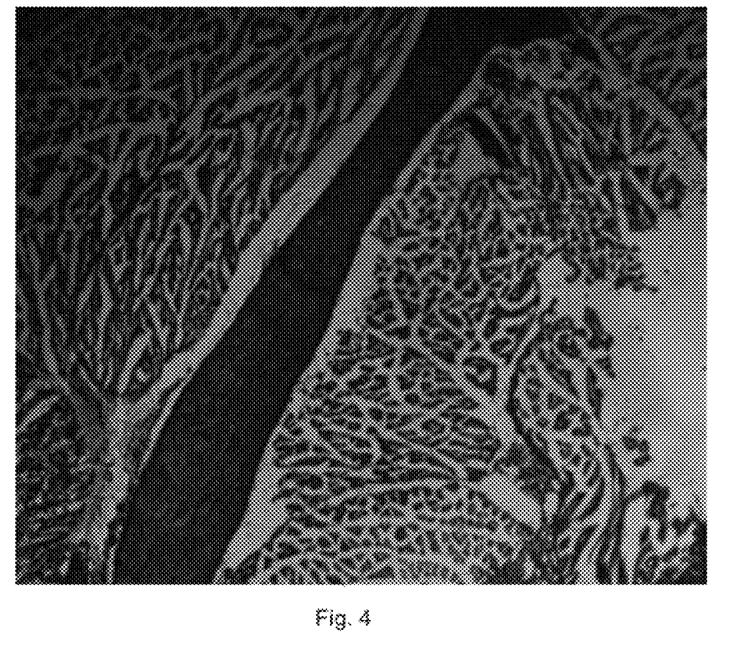
FIG. 4 illustrates photographs showing Black and Gold staining confirmed the in vitro staining of the sciatic nerve.

As shown in FIG. 3, BDB selectively stained the sciatic nerve of a wild-type mouse in vitro. The staining of the sciatic nerve was confirmed by the Black and Gold staining of the adjacent tissue section (see FIG. 4).

Following in vitro studies, we investigated the ability of BDB to monitor myelin contents ex vivo in the mouse.

Ex Vivo Staining Procedure: (1) Injection of BDB via tail vein in wild type mouse; (2) Removal of sciatic nerve imbedded in muscle from right side; (3) Sectioning of muscle with nerve; (4) Observation of tissue under microscope to check staining; (5) Removal of left sciatic nerve from muscle; and (6) Observation of fluorescent in FLI machine.

Ex Vivo Results

Figure 5:
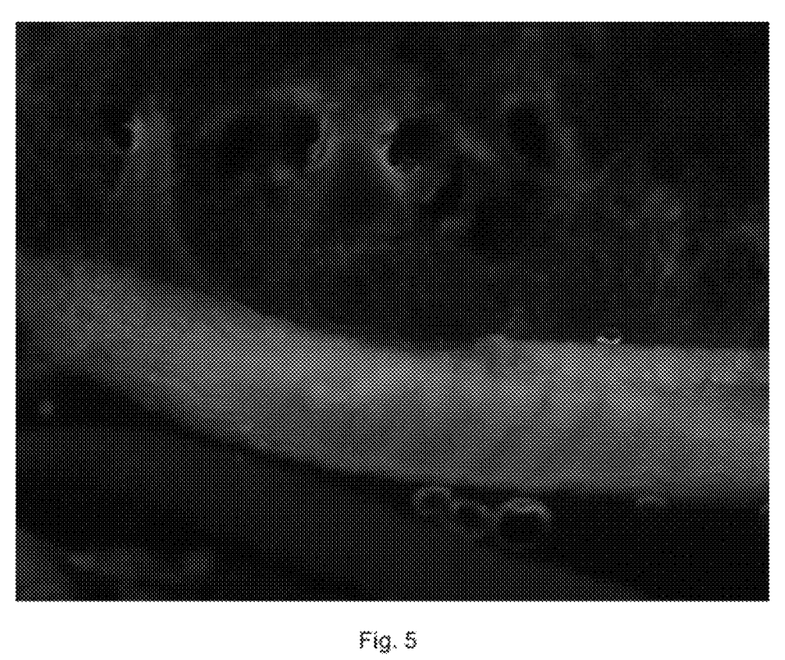
FIG. 5 illustrates a photograph showing that the sciatic nerve was successfully stained ex vivo post injection.
Figure 6:
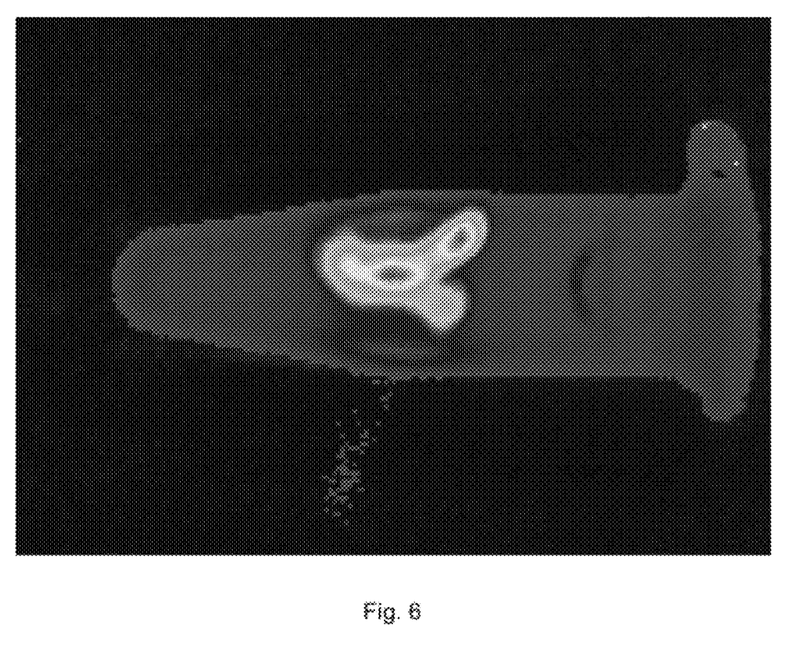
FIG. 6 illustrates that the FLI machine picked up fluorescence from sciatic nerve placed in a tube with 4% PFA (paraformaldehyde) solution.
Figure 7:
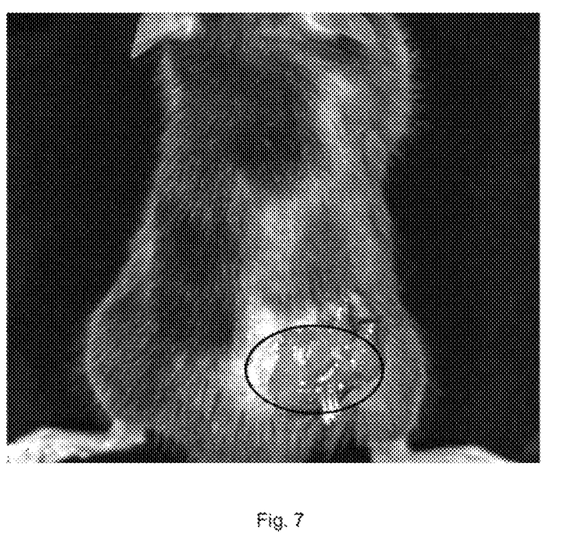
FIG. 7 illustrates a photograph showing that the sciatic nerve was successfully exposed in mouse.
Figure 8:
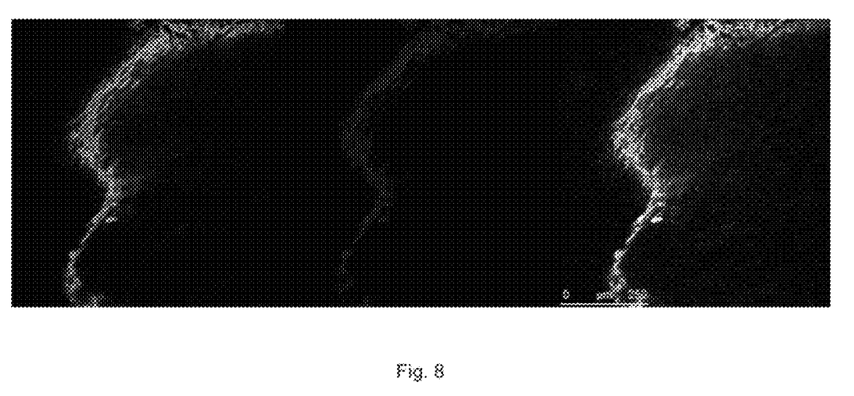
FIG. 8 illustrates a photograph showing that a multiphoton microscope was able to detect the sciatic nerve while the animal was alive in blue and green channel.

As shown in FIG. 5, the sciatic nerve was successfully stained post injection. An FLI machine picked up fluorescence from sciatic nerve placed in a tube with 4% paraformaldehyde (PFA) solution (FIG. 6).

In Vivo Staining Procedure: (1) Shave fur off region where sciatic nerve is located; (2) Cut soft tissue and muscle tissue covering sciatic nerve using surgical scissors; (3) Place animal under multiphoton microscope while anesthetized with isoflurane gas; and (4) Take live images of nerve.

In Vivo Results

As shown in FIG. 5, the sciatic nerve was successfully exposed in mouse and multiphoton microscope was used to image the sciatic nerve while animal was alive in blue and green channel.

CONCLUSION

Based on the above in vitro, ex vivo and in vivo studies, we have demonstrated that the fluorescent probe BDB can be used as a specific histochemical stain for PNS myelin in a wild type mouse model. While all techniques used were fluorescence based, a human applicable method can include BDB that has been radiolabeled to image CNS myelin for Positron Emission Tomography (PET).

All references cited herein, including patents, patent applications, papers, text books, and the like, and the references cited therein, to the extent that they are not already, are hereby incorporated herein by reference in their entirety. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Having described the invention, the following is claimed:

1. A method of labeling myelinated regions in an animal's peripheral nervous system in vivo, the method comprising:
   administering to the animal's peripheral nervous system tissue a molecular probe including the general formula:

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, or alkyl derivatives thereof, or derivatives thereof that include a radiolabel, a chelating group, a near infrared imaging group, or a salt; and detecting the molecular probe bound to myelin of the peripheral nervous system to determine myelinated regions of the animal's peripheral nervous system.

2. The method of claim 1, further comprising the step of administering the molecular probe to the animal parenterally.

3. The method of claim 1, the radiolabel including a positron emitting $^{11}C$ and a positron emitting $^{18}F$.

4. The method of claim 1, wherein $R_1$ and $R_2$ are amines or alkyl derivatives thereof or radiolabeled derivatives thereof.

5. A method of detecting myelin in vivo in an animal's peripheral nervous system tissue, the method comprising:
   (i) administering to the animal a molecular probe including the general formula:

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, or alkyl derivatives thereof, or derivatives thereof that include a radiolabel, a chelating group, a near infrared imaging group, or a salt;
   (ii) visualizing the animal's peripheral nervous system tissue using an in vivo imaging modality to determine the distribution of the molecular probe bound to myelin of the animal's peripheral nervous system.

6. The method of claim 5, the in vivo imaging modality comprising a Positron Emission Tomography (PET) imaging modality or micro Positron Emission Tomography (micro-PET) imaging modality.

7. The method of claim 5, further comprising the step of administering the molecular probe to the animal parenterally.

8. The method of claim 5, the radiolabel including a positron emitting $^{11}C$ and a positron emitting $^{18}F$.

9. The method of claim 5, wherein $R_1$ and $R_2$ are amines or alkyl derivatives thereof or radiolabeled derivatives thereof.

10. A method of imaging myelinated tissue at a surgical site in an animal comprising the steps of:
    (i) administering to tissue at a surgical site of an animal that includes myelin of the peripheral nervous system a molecular probe having the general formula:

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, or alkyl derivatives thereof, or derivatives thereof that include a radiolabel, a chelating group, a near infrared imaging group, or a salt thereof; and
    (ii) visualizing using an in vivo imaging modality a distribution of the molecular probe bound to myelin of the peripheral nervous system at the surgical site in the animal.

11. The method of claim 10, the radiolabel including a positron emitting $^{11}C$ and a positron emitting $^{18}F$.

12. The method of claim 10, wherein $R_1$ and $R_2$ are amines or alkyl derivatives thereof or radiolabeled derivatives thereof.

13. The method of claim 10, wherein the surgical site is an open surgical field or a minimally invasive field created by incising the tissue.

14. The method of claim 10, wherein the administering step comprises topical application of the molecular probe subsequent to incising tissue in the creation of a surgical site.

15. The method of claim 14 wherein the molecular probe is dissolved or suspended in a solution suitable for surgical irrigation.

16. The method of claim 10 wherein the administering step comprises parenteral administration of the molecular probe prior to creation of the surgical site.

* * * * *

UNITED STATES PATENT AND TRADEMARK OFFICE
CERTIFICATE OF CORRECTION

PATENT NO. : 9,555,130 B2
APPLICATION NO. : 13/284288
DATED : January 31, 2017
INVENTOR(S) : Yanming Wang et al.

Page 1 of 1

It is certified that error appears in the above-identified patent and that said Letters Patent is hereby corrected as shown below:

In the Specification

Column 1, after Line 12 insert:

--GOVERNMENT FUNDING
This invention was made with government support under Grant No. NS061837 awarded by The National Institute of Health. The United States government has certain rights in the invention.--

Signed and Sealed this
Twelfth Day of December, 2017

Joseph Matal
*Performing the Functions and Duties of the
Under Secretary of Commerce for Intellectual Property and
Director of the United States Patent and Trademark Office*